United States Patent [19]
Slootsky

[11] Patent Number: 5,645,421
[45] Date of Patent: Jul. 8, 1997

[54] ORTHODONTIC APPLIANCE DEBONDER

[75] Inventor: Gary Lee Slootsky, Clarence, N.Y.

[73] Assignee: Great Lakes Orthodontics Ltd., Tonawanda, N.Y.

[21] Appl. No.: 430,441

[22] Filed: Apr. 28, 1995

[51] Int. Cl.⁶ .................................................. A61C 3/00
[52] U.S. Cl. ...................................... 433/6; 433/3; 433/2
[58] Field of Search ............................. 433/2, 3, 4, 5, 433/6, 7, 152, 154, 158, 161, 222.1

[56] References Cited

U.S. PATENT DOCUMENTS

| | | | |
|---|---|---|---|
| 2,464,289 | 3/1949 | Border | 32/43 |
| 3,460,254 | 8/1969 | Scheuer | 32/14 |
| 3,747,215 | 7/1973 | Joyner | 32/13 |
| 4,379,693 | 4/1983 | Wallshein | 433/7 |
| 4,402,671 | 9/1983 | Westerman | 433/152 X |
| 4,417,876 | 11/1983 | Lynch | 433/161 |
| 4,424,032 | 1/1984 | Howe | 433/19 |
| 4,431,411 | 2/1984 | Witzig | 433/6 |
| 4,472,138 | 9/1984 | Howe | 433/19 |
| 4,573,914 | 3/1986 | Nord | 433/7 X |
| 5,009,597 | 4/1991 | Schaefer | 433/222.1 X |
| 5,362,232 | 11/1994 | Franseen et al. | 433/9 |
| 5,366,372 | 11/1994 | Hansen et al. | 433/4 |

*Primary Examiner*—Nicholas D. Lucchesi
*Attorney, Agent, or Firm*—Hodgson, Russ, Andrews, Woods & Goodyear LLP

[57] ABSTRACT

An orthodontic appliance debonder for minimizing the time and effort on the part of the clinician in removing bondable orthodontic appliances, i.e. those having a plastic body secured to the crowns of the teeth by an orthodontic bonding agent. In accordance with the invention, a screw is incorporated in the plastic body of the appliance, in particular in the occlusal portion thereof. The screw is oriented substantially vertically when the patient's head is in an upright position and preferably is positioned over the first molar. A thin layer of plastic occlusal to the screw maintains the integrity of the seal between the plastic body and the tooth. This thin layer of plastic is compromised when the screw is activated, such as being turned or rotated by an Allen wrench type tool, thus breaking the bond or seal between the plastic body and the tooth. The appliance lifts up in a manner similar to a car being lifted up by a screw type jack. Installation of the debonding screw in the appliance results in a slightly thicker occlusal plastic, but this is clinically inconsequential in most cases.

9 Claims, 3 Drawing Sheets

ORTHODONTIC APPLIANCE DEBONDER

BACKGROUND OF THE INVENTION

This invention relates to the art of orthodontics, and more particularly to orthodontic appliances having new and improved debonding means and a method of making the same.

The area of use of the present invention is with orthodontic appliances of the type having a molded plastic body secured to the crowns of the teeth by an orthodontic bonding agent. Such appliances which apply corrective forces to the teeth are known in the art as bonded-style Herbst appliances and bonded style Rapid Palatal Expanders (RPE). When the orthodontic treatment is completed it is necessary to remove the plastic body which was glued or bonded to the patient's teeth. This typically has been done using orthodontic tools either to pry off the plastic body from the teeth or to cut or section the plastic body to facilitate its removal. While some orthodontists are able to use such removal techniques with success, there is the possibility of such techniques being time consuming and difficult thereby causing discomfort or distress to the patient.

It would therefore be highly desirable to provide an orthodontic appliance of the type having a plastic body bonded to the teeth and provided with a debonding means affording quick and easy removal of the plastic body in a manner avoiding discomfort and distress to the patient.

SUMMARY OF THE INVENTION

It is, therefore, a primary object of this invention to provide an orthodontic appliance having a new and improved debonding means.

It is a more particular object of this invention to provide an orthodontic appliance of the type having a plastic body secured to the patient's teeth by a bonding agent which appliance incorporates a new and improved debonding means.

It is a further object of this invention to provide such an orthodontic appliance wherein the debonding means affords quick and easy removal of the plastic body from the teeth in a manner avoiding discomfort and distress to the patient.

The present invention provides a debonder for an orthodontic appliance of the type including a plastic body having a first surface bonded to a patient's tooth and a second surface spaced therefrom to define the thickness of the body. The debonder comprises screw means carried in the plastic body and having a first end spaced inwardly from the first surface and having a second, opposite end provided with a formation engageable by a tool so that upon rotation by the tool the screw means is advanced toward and through the first surface of the plastic body and the first end of the screw means engages the tooth causing the screw means to apply a lifting force to the plastic body to break the bond between the first surface of the body and the tooth thereby allowing quick and easy removal of the appliance from the tooth.

The foregoing and additional advantages and characterizing features of the present invention will become clearly apparent upon a reading of the ensuing details description together with the included drawing wherein:

BRIEF DESCRIPTION OF THE DRAWING FIGURE

DETAILED DESCRIPTION OF THE ILLUSTRATED EMBODIMENT

The present invention is directed to minimizing the time and effort on the part of the clinician in removing bondable orthodontic appliances, i.e. those having a plastic body secured to the crowns of the teeth by an orthodontic bonding agent. In accordance with the invention, a screw is incorporated in the plastic body of the appliance, in particular in the occlusal portion thereof. The screw is oriented substantially vertically when the patient's head is in an upright position and preferably is positioned over the first molar. A thin layer of plastic occlusal to the screw maintains the integrity of the seal between the plastic body and the tooth. This thin layer of plastic is compromised when the screw is activated, such as being turned or rotated by an Allen wrench type tool, thus breaking the bond or seal between the plastic body and the tooth. The appliance lifts up in a manner similar to a car being lifted up by a screw type jack. Installation of the debonding screw in the appliance results in a slightly thicker occlusal plastic, but this is clinically inconsequential in most cases.

The debonder of the present invention is for use with bonded style Herbst appliances and with bonded style Rapid Palatal Expanders (RPE). Bonded style Herbst appliances are shown, for example, in U.S. Pat. Nos. 4,424,032 issued Jan. 3, 1984 and 4,472,138 issued Sept. 18, 1984, both entitled "Orthodontic Appliance", the disclosures of which are hereby incorporated by reference.

Figure 1:
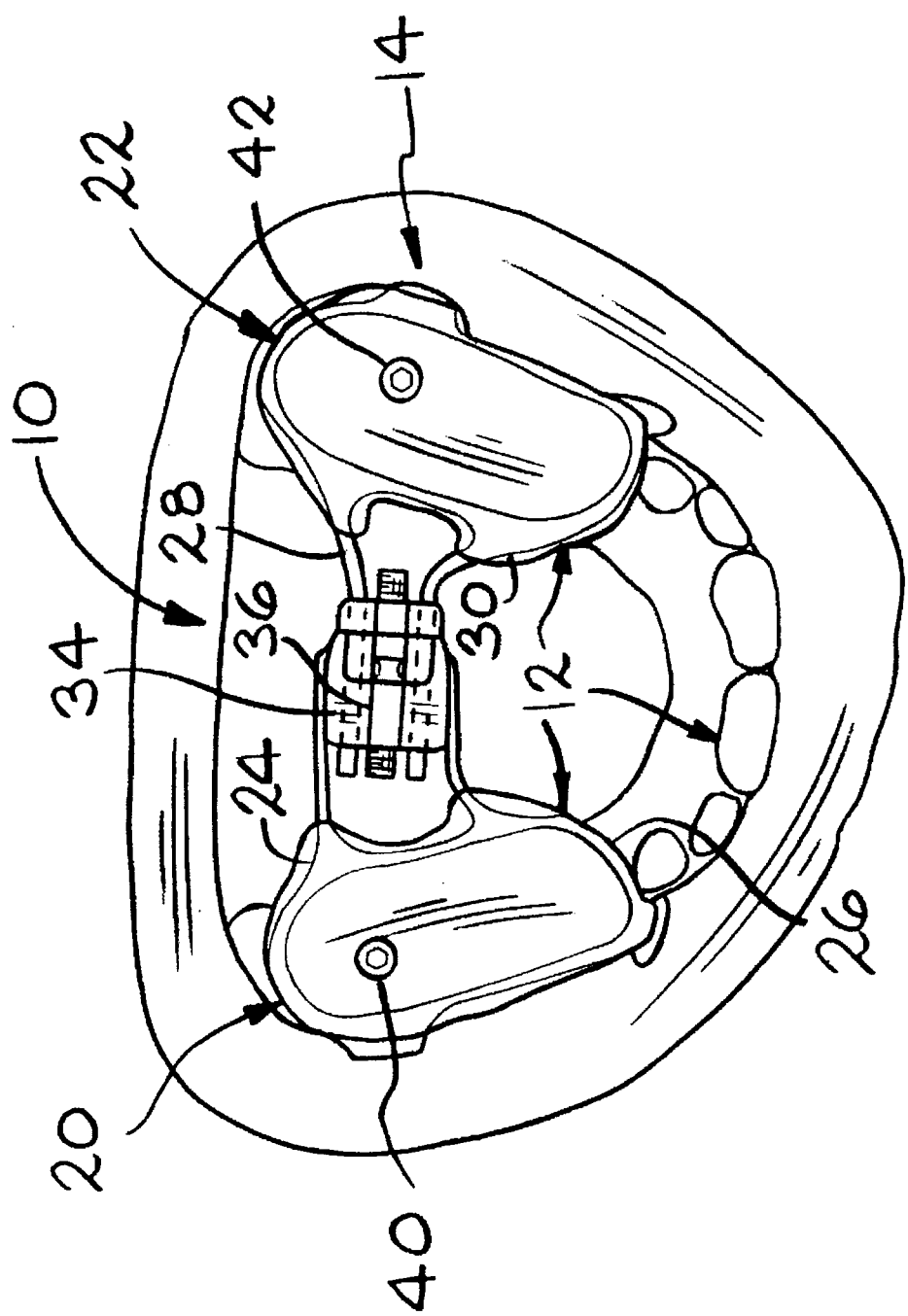
FIG. 1 is a plan view of an orthodontic appliance provided with a debonding means according to the present invention.

A bondable orthodontic appliance provided with a debonder according to the present invention is shown in FIG. 1. The appliance, generally designated 10, is operatively positioned on a dental arch 12 which, for convenience in illustration, is part of a dental study model 14. The appliance 10 comprises a pair of molded plastic or acrylic bodies 20 and 22 secured to the crowns of teeth of the arch 12 by an orthodontic bonding agent or glue (not shown in FIG. 1). The bodies 20 and 22 are on opposite sides of the dental arch 12 and are joined by an arrangement or framework of wires 24, 26, 28 and 30 the outer end portions of which are embedded in the plastic bodies 20, 22 and the inner ends of which are joined to a screw-type expander mechanism 34. The appliance 10 thus described is well-known to those skilled in the art, and rotation or turning of a screw 36 located generally centrally in mechanism 34 applies lateral outward force as viewed in FIG. 1 in both directions through wires 24, 26, 28 and 30 to the plastic bodies 20 and 22 to apply orthodontically corrective forces to the teeth of the arch 12. Thus, mechanism 34 and wires 24, 26, 28 and 30 are conventional and form no part of the present invention.

Figure 2:
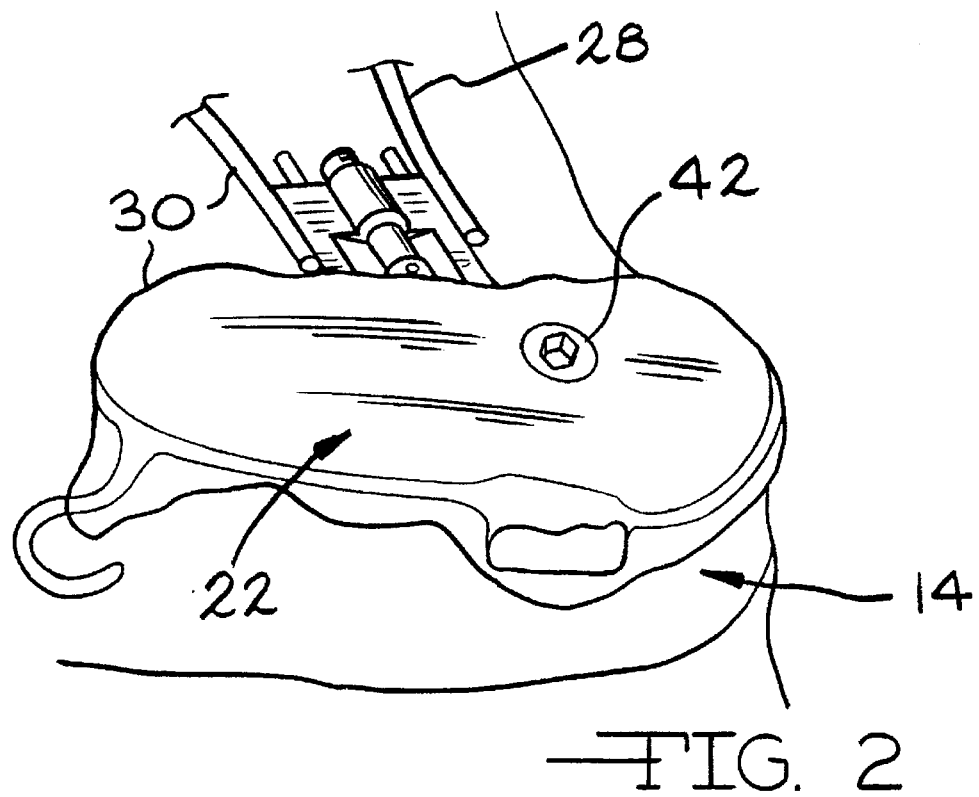
FIG. 2 is an enlarged perspective view of a portion of the appliance of FIG. 1 and showing the debonding means in further detail.

The debonder of the present invention comprises screw means incorporated or carried in the plastic body of the appliance, in particular screw 40 in body 20 and screw 42 in body 22 as shown in FIG. 1. According to a preferred mode of the present invention, each screw 40 and 42 is at a location along the corresponding body 20 and 22, respectively, so as to be over the first molar when the appliance 10 is in operative position on the dental arch 12 as shown in FIG. 1. In addition, each screw 40, 42 is oriented with the longitudinal axis thereof generally perpendicular to a plane including the occlusal surface of the tooth. As shown in FIG. 1 and in the enlargement of FIG. 2, each screw 40, 42 has an end at the outer surface of the corresponding body 20, 22 which is accessible for operation in a manner which will be described.

Figure 3:
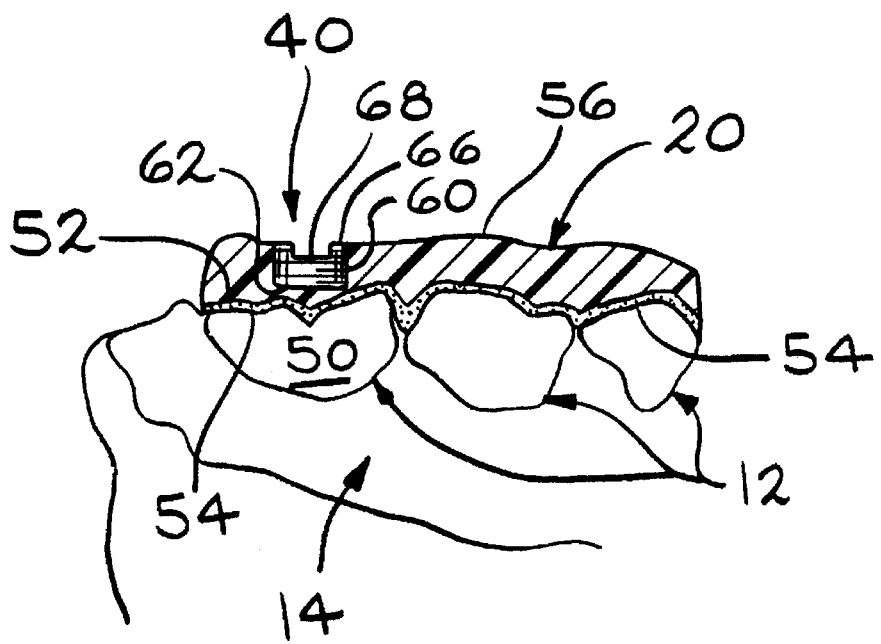
FIG. 3 is a sectional view, partly diagrammatic, of a portion of the appliance of FIG. 1 and showing the debonding means in further detail.

One of the screw means, for example screw 40, is shown in greater detail in FIG. 3, it being understood that the other screw means 42 is identical. The appliance body 20 is operatively associated with a plurality of teeth, one of which is the first molar 50. Body 20 includes a first surface 52 which is bonded or sealed to the patient's teeth by a bonding agent or glue designated 54 in FIG. 3. By way of example, the bonding agent or glue can comprise a bonding adhesive commercially available from Reliance Orthodontics Inc. of Itasca, Ill. under the registered trademark EXCEL. Body 20 has a second surface 56 spaced from first surface 52 thereby defining the thickness of body 20 as seen in FIG. 3. Body 22 is of similar structure and likewise located and bonded to its corresponding teeth. Screw means 40 is provided with threads 60 along the axial length thereof and has a first, relatively flat end 62 spaced inwardly in body 20 a short distance from surface 52. This insures that the integrity of the seal or bond between the tooth and plastic body 20 is maintained. The distance or spacing between end 62 and surface 52 is exaggerated for purposes of illustration in FIG. 3, whereas in actual practice it can be quite small, in the nature of a film thickness so Song as the aforementioned seal integrity is maintained. Screw means 40 is oriented with the longitudinal axis thereof extending between surfaces 52 and 56 as viewed in FIG. 3. Expressed differently, the longitudinal axis of screw means 40 is substantially perpendicular to a plane extending along the occlusal surface of tooth 50 and is substantially parallel to the direction of the roots of tooth 50.

Screw means 40 has a second, opposite end 66 provided with a formation 68 therein for engagement by a tool, for example by the end of an Allen-type wrench as will be described. According to a preferred mode of the present invention end 66 and formation 688 are exposed and not covered by the plastic of body 20. If for any reason end 66 was set inwardly of surface 56 so as to be covered, it would be necessary to remove material to expose formation 68 in order to initiate the debonding action of screw means 40. In the preferred arrangement shown in FIG. 3, end 66 of screw means 40 is substantially flush with surface 56 of body 20. Screw means 42 is identical in structure, location and operation to screw means 40. By way of example, in an illustrative appliance, each screw means 40, 42 comprises a stainless steel screw having a length of 0.135 inch and a diameter of 0.162 inch. Each body 20, 22 is of acrylic material having a thickness slightly greater than the length of the corresponding screw means 40, 42.

Figure 4:
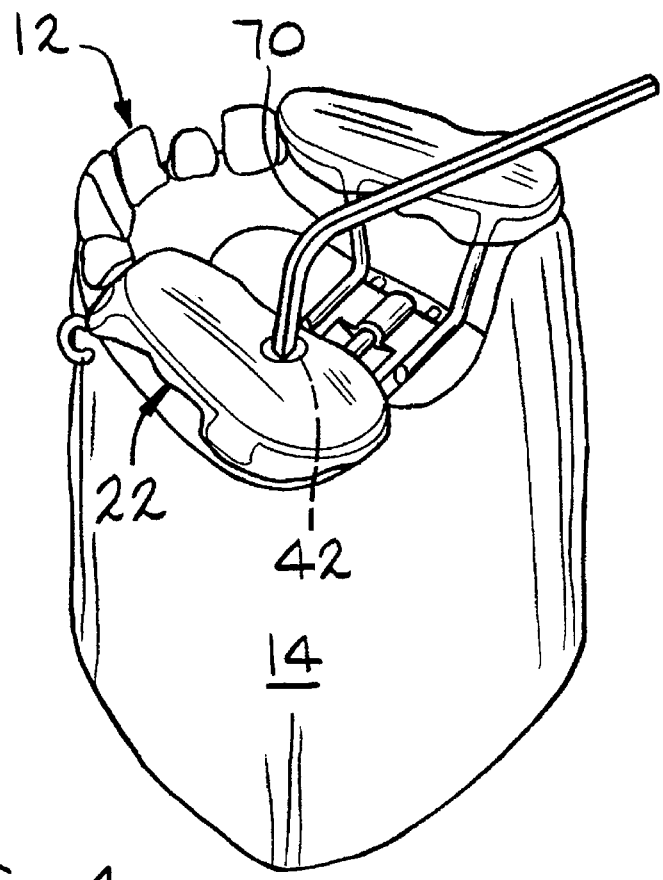
FIG. 4 is a perspective view of the appliance of FIG. 1 and showing the manner in which the debonding means is operated.
Figure 5:
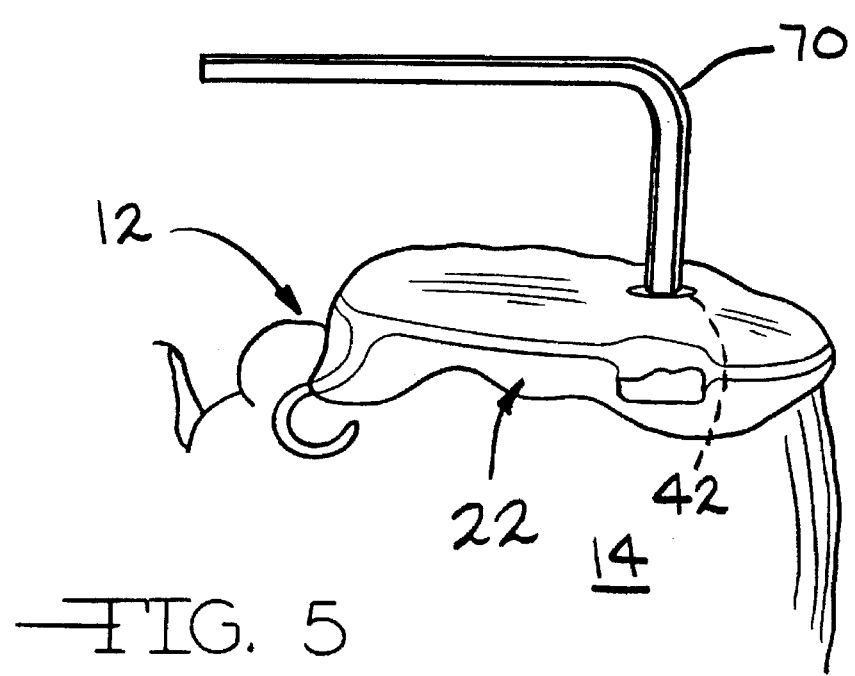
FIG. 5 is a side elevational view of the appliance of FIG. 1 further illustrating operation of the debonding means.

The appliance 10 is positioned on the teeth of a patient in a manner similar to the way it is shown positioned on the dental study model or work model shown in FIG. 1. The appliance 10 is used for treatment on either upper or lower dental arches of patients. The plastic bodies 20 and 22 are bonded or sealed to the teeth of the arch in a known manner using an orthodontic bonding adhesive such as that previously described. Then, mechanism 34 is adjusted in a known manner to apply the desired corrective orthodontic forces to the teeth of the arch. When the orthodontic treatment is completed, which may take an extended period of time, the plastic bodies 20, 22 must be separated from the teeth of the arch. This is done quickly and easily by simply inserting the end of a small Allen wrench designated 70 in FIGS. 4 and 5 to turn or rotate each screw 40 and 42, one at a time, thereby advancing each screw through its respective plastic body 20, 22 so that the screw engages its respective tooth and applies a lifting face to break the seal or bond between the corresponding plastic body and tooth. FIGS. 4 and 5 show the wrench 70 at various stages of tuning and advancing screw means 42 in body 22. The debonder of the present invention advantageously provides convenient, rapid and easy removal of bonded orthodontic appliances from teeth thereby avoiding any discomfort or disturbance to the patient.

While the preferred form of debonding means includes a single screw in each plastic body of the appliance 10, an additional one or more screws occlusal to other teeth along the arch can be employed if desired.

The following is a description of a preferred method for fabricating a bonded orthodontic appliance such as that designated 10 in FIG. 1. Upper and lower models are articulated to the patient's bite in an articulator, and the wire framework such as that designated 24, 26, 28 and 30 in FIG. 1 is completed. The upper model is detailed from the articulator and supporting foil is applied to the upper model. The heads of the debonding screws 40, 42 are protected by filling the formation with wax. Next the debonding screws are positioned over selected maxillary teeth by applying a film of cold curing acrylic on the occlusal surfaces of the model teeth and placing the flat ends of the screws on the acrylic coated surface. Next, the upper model with debonding screws is placed in a conventional pressure pot for curing. Then the upper model is placed in a dental forming machine of the type commercially available under the name BIOSTAR. For a more detailed description of a method for making an orthodontic appliance using such machine, reference may be made to U.S. Pat. Nos. 3,768,164 issued Oct. 30, 1973 and 4,798,534 issued Jan. 17, 1989 the disclosures of which are hereby incorporated by reference.

The wire framework is replaced onto the upper model, an additional amount of cold curing acrylic is placed around wire framework as well as debonding screws, and a 2 mm or 3 mm blank of SPUNT BIOCRYL material is formed over the upper model. The appliance then is removed and appliance is trimmed in a usual fashion. Then the upper model is returned to the articulator. The occlusal portion of the appliance is adjusted as needed. The appliance is polished, protective wax is steamed out of the debonding screw head, and the appliance is disinfected.

It is therefore apparent that the present invention accomplishes its intended objects. While an embodiment of the present invention has been described in detail, that is for the purpose of illustration, not limitation.

What is claimed is:

1. In an orthodontic appliance including a plastic body having a first continuous surface adapted to be bonded to a patient's tooth and a second surface spaced therefrom to define a thickness of the body, the improvement comprising a debonder comprising screw means carried in said body and having a first end spaced inwardly from said first surface and having a second, opposite end provided with a formation engageable by a tool so that upon rotation by the tool to advance said screw means through said body and toward and through said first surface said first end of said screw means engages the tooth causing said screw means to apply a lifting force to said body to break the bond between said first surface of said bond and the tooth thereby allowing removal of the appliance from the tooth.

2. The appliance of claim 1 wherein said second end of said screw means is exposed adjacent said second surface of said body.

3. The appliance of claim 1, wherein said screw means is oriented with the longitudinal axis thereof extending between said first and second surfaces of said body.

4. The appliance of claim 1, wherein said body is adapted to extend along a plurality of teeth and said screw means is located for engagement with the first molar.

5. The appliance of claim 1, wherein said formation on said second end of said screw means is shaped to receive the end of an Allen wrench.

6. The appliance of claim 1, wherein said first end of said screw means is flat.

7. A method of making an orthodontic appliance of the type having a plastic body adapted to be bonded to a patient's teeth and incorporating an improved debonding means, said method comprising:

a) providing a dental model of an arch of the patient's teeth;

b) providing a debonding means in the form of a set screw flat on one end and having a tool-engaging formation on the opposite end;

c) applying a thin layer of plastic material to an occlusal surface of the model teeth;

d) placing the flat end of the set screw on the layer of plastic material; and e) forming the plastic body of the appliance on the model in a manner incorporating the set screw in the body such that the flat end is within the body and the tool-engaging formation at the opposite end of the set screw is exposed.

8. An orthodontic method comprising the steps of:

a) providing an orthodontic appliance of the type having a plastic body for bonding to the teeth of a patient and having debonding screw means in said body;

b) installing the appliance on the teeth of a patient with the debonding screw means facing a tooth surface and with the plastic body bonded to the teeth by a bonding agent.

c) performing an orthodontic treatment on the patient's teeth using the appliance; and removing the appliance from the patient's teeth by advancing the debonding screw through the plastic body so that an end of the screw engages the surface of the tooth causing the screw to apply a lifting force to the plastic body to break the bond between the body and the tooth.

9. In an orthodontic appliance including a plastic body having a first surface adapted to be bonded to a patient's tooth and a second surface spaced therefrom to define a thickness of the body, the improvement comprising a debonder comprising screw means carried in said body and having a first end spaced inwardly from said first surface and having a second, opposite end provided with a formation engageable by a tool, said thickness of said plastic body bring greater than the distance between said first and second ends of said screw means, so that upon rotation by the tool to advance said screw means toward and through said first surface said first end of said screw means engages the tooth causing said screw means to apply a lifting force to said body to break the bond between said first surface of said body and the tooth thereby allowing removal of the appliance from the tooth.

* * * * *